US007939055B2

(12) United States Patent
Schneider et al.

(10) Patent No.: US 7,939,055 B2
(45) Date of Patent: May 10, 2011

(54) POLYMERIC AROMATIC N-HALO SULFONAMIDES

(76) Inventors: Charles A. Schneider, Villa Hills, KY (US); David J. Schneider, Union, KY (US)

(*) Notice: Subject to any disclaimer, the term of this patent is extended or adjusted under 35 U.S.C. 154(b) by 1085 days.

(21) Appl. No.: 11/688,296

(22) Filed: Mar. 20, 2007

(65) Prior Publication Data
US 2007/0160565 A1 Jul. 12, 2007

Related U.S. Application Data

(63) Continuation-in-part of application No. 10/369,175, filed on Feb. 18, 2003, now Pat. No. 7,465,829.

(51) Int. Cl.
*A61K 31/74* (2006.01)
(52) U.S. Cl. ............... 424/78.27; 424/78.26; 424/78.08
(58) Field of Classification Search ............... 424/78.27, 424/78.26, 78.08
See application file for complete search history.

(56) References Cited

U.S. PATENT DOCUMENTS

| 3,888,897 | A  | 6/1975  | Martin |
| 6,296,841 | B1 | 10/2001 | Schneider |
| 6,667,030 | B1 | 12/2003 | Schneider |
| 6,743,420 | B2 | 6/2004  | Schneider |
| 2005/0058615 | A1 | 3/2005 | Schneider et al. |
| 2005/0100526 | A1 | 5/2005 | Uhrich |
| 2005/0287109 | A1 | 12/2005 | Schneider et al. |
| 2006/0029568 | A1 | 2/2006 | Kurtz et al. |
| 2006/0280766 | A1 | 12/2006 | Schneider et al. |
| 2007/0036743 | A1 | 2/2007 | Plochocka et al. |

OTHER PUBLICATIONS

Emerson,"Slow Release of Active Chlorine and Bromine from Styrene-Divinylbenzene Copolymers Bearing N,N-Dichlorosulfonamide, N-Chloro -N -alkyIsulfonamide, and N- Bromo- N-alkyIsulfonamide Functional Groups. Polymer-Supported Reagents", 1991, Ind. Eng. Chem. Res., 30, pp. 2426-2430.*
International Search Report dated Jun. 27, 2008.
Bozkurt, Ayhan, "Anhydrous Proton Conductive Polystyrene Sulfonic Acid Membranes", Turk J Chem, 29 (2005), 117-123.
FDA, Dry Milk Ordinance Supplement 1 Appendix B pp. 87-88 (1995).
Mullen, The Biocides Business: Regulation, Safety and Applications, pp. 251-266 (2002).
Dawson et al., Inter. Ass. Fish & Wildlife, Approval of Drugs for Public Fish Production, Second Mids-Year Report of Progress, pp. 1-11, (1996).

* cited by examiner

*Primary Examiner* — Michael G Hartley
*Assistant Examiner* — James W Rogers
(74) *Attorney, Agent, or Firm* — Fay Sharpe LLP; Richard M. Klein

(57) ABSTRACT

A polymer comprises a monomer having a N-halo sulfonamide pendant group and having the formula:

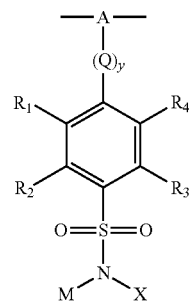

Formula (I)

wherein A is a trivalent linkage;
wherein Q is a divalent linkage and y is 0 or 1;
wherein $R_1$, $R_2$, $R_3$, and $R_4$ are as described within;
wherein X is halogen; and
wherein M is an alkali or alkaline earth metal.
In specific embodiments, $R_1$, $R_2$, $R_3$, and $R_4$ are hydrogen; X is chlorine; and M is sodium or potassium.

39 Claims, No Drawings

POLYMERIC AROMATIC N-HALO SULFONAMIDES

CROSS-REFERENCE TO RELATED APPLICATIONS

The present application is a continuation-in-part application of U.S. patent application Ser. No. 10/369,175, filed Feb. 18, 2003, which application claims priority from U.S. Provisional Application Ser. No. 60/357,265, filed Feb. 19, 2002. The present application is also a continuation-in-part application of U.S. patent application Ser. No. 11/506,737, filed Aug. 18, 2006, which claims priority from U.S. Provisional Application Ser. No. 60/709,919, filed Aug. 19, 2005, and is also a continuation-in-part of U.S. patent application Ser. No. 11/216,495, filed Aug. 31, 2005, which is a continuation-in-part application of U.S. patent application Ser. No. 10/369,175, filed Feb. 18, 2003, which application claims priority from U.S. Provisional Application Ser. No. 60/357,265, filed Feb. 19, 2002.

BACKGROUND

Halo active aromatic sulfonamide compounds have enhanced biocidal properties and minimal side effects. They can be used to arrest or kill the growth of living organisms, particularly microorganisms, and may also be used as a fungicide or pesticide. In U.S. Pat. Nos. 6,296,841; 6,743,420; and 6,667,030, the use of Chloramine-T (the sodium salt of N-chloro-p-toluenesulfonamide) as an odor control agent is also described.

In use, the halo active aromatic sulfonamide compound is generally dissolved in a medium in which it is soluble. The medium can be a gaseous, solvent, solid formulation, or aqueous medium, and the sulfonamide compound becomes an integral part of the medium such that it cannot easily be separated from the medium. The resulting solution is brought into contact with another medium (which can again be a solid, solvent, water, or gas) affected by microorganisms. This contact is usually affected by spraying, washing, dipping, and/or mixing in such a manner as to contact the affected area, surface, or substrate with an aqueous formulation of the desired sulfonamide compound or a blended mixture of same. Because the sulfonamide compound cannot easily be separated from the medium, it is generally discarded after use. The opportunity to regenerate and/or reuse the sulfonamide compound is thus lost.

It would be desirable to provide a halo active aromatic sulfonamide compound which can be separated from the medium in which it is normally dissolved after it has performed its function. It would also be desirable if the halo active aromatic sulfonamide compound could be regenerated and/or reused.

BRIEF DESCRIPTION

Disclosed herein, in various embodiments, are polymers which comprise an aromatic N-halo sulfonamide pendant group. The polymer allows the active aromatic N-halo sulfonamide moiety to contact and/or react with various species contained in a solvent, aqueous media, or gaseous media, and remain separable from such media. The aromatic N-halo sulfonamide pendant group may then be regenerated.

In specific embodiments, the aromatic N-halo sulfonamide moiety is directly connected to the polymeric backbone. In other embodiments, the aromatic N-halo sulfonamide moiety is connected to the polymeric backbone by a divalent linkage.

In further specific embodiments, the aromatic N-halo sulfonamide moiety is connected to the polymeric backbone by an ester linkage.

The polymer comprises a monomer of the following Formula (I):

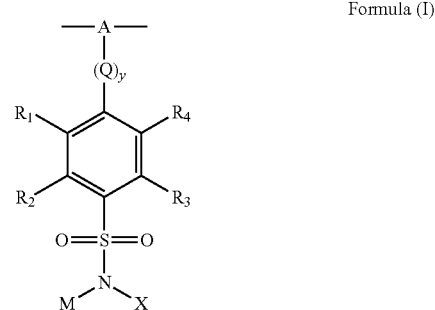

Formula (I)

wherein A is a trivalent linkage;
wherein Q is a divalent linkage and y is 0 or 1;
wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen; and
wherein M is an alkali or alkaline earth metal.

In specific embodiments, y is 1 and Q comprises an ester linkage.

In other specific embodiments, $R_1$, $R_2$, $R_3$, and $R_4$ are independently selected from hydrogen or alkyl from $C_1$ to $C_{12}$; X is chlorine, bromine, fluorine, or iodine; and M is sodium or potassium. In a further embodiment, $R_1$, $R_2$, $R_3$, and $R_4$ are hydrogen; X is chlorine; and M is sodium or potassium.

In specific embodiments, the polymer comprises only monomers of Formula (I).

In further embodiments, the monomer has the following Formula (III):

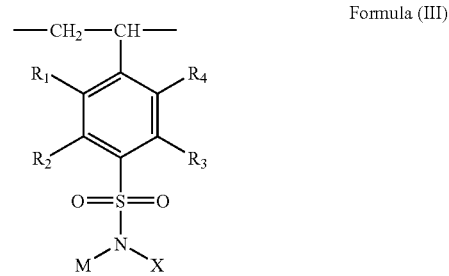

Formula (III)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen; and
wherein M is an alkali or alkaline earth metal.

In specific embodiments, the polymer comprises only monomers of Formula (III).

In further embodiments, the monomer has the following Formula (V):

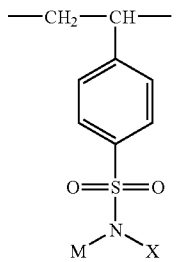

Formula (V)

wherein X is chlorine, bromine, fluorine, or iodine; and
M is an alkali or alkaline earth metal.

In further embodiments, X is chlorine and M is sodium or potassium.

In specific embodiments, the polymer comprises only monomers of Formula (V).

In further embodiments, the monomer has the following Formula (VII):

Formula (VII)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen; and
wherein M is an alkali or alkaline earth metal.

In a further embodiment, $R_1$, $R_2$, $R_3$, and $R_4$ are hydrogen or alkyl from $C_1$ to $C_{12}$; X is chlorine, bromine, fluorine, or iodine; and M is sodium or potassium.

In a further embodiment, $R_1$, $R_2$, $R_3$, and $R_4$ are hydrogen; X is chlorine; and M is sodium or potassium.

In specific embodiments, the polymer comprises only monomers of Formula (VII).

In further embodiments, the monomer has the following Formula (IX):

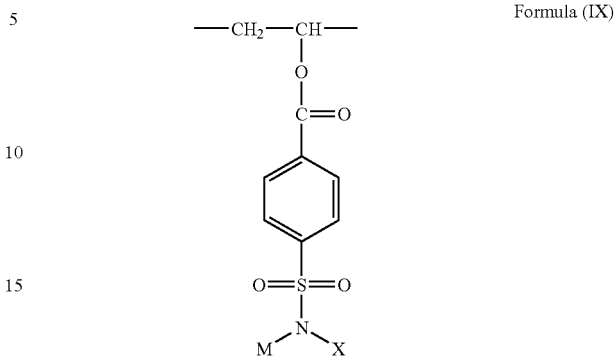

Formula (IX)

wherein X is chlorine, bromine, fluorine, or iodine; and
M is an alkali or alkaline earth metal.

In further embodiments, X is chlorine and M is sodium or potassium.

In specific embodiments, the polymer comprises only monomers of Formula (IX).

In further embodiments, the polymer further comprises a monomer of the following Formula (XI):

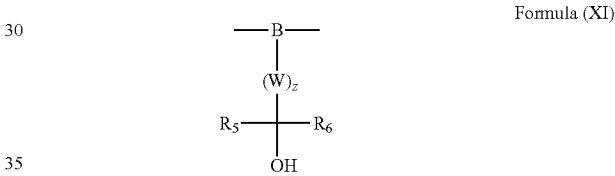

Formula (XI)

wherein B is a trivalent linkage;
wherein W is a divalent linkage and z is 0 or 1; and
wherein $R_5$ and $R_6$ are independently selected from linear or branched alkyl from $C_1$ to $C_{12}$.

In specific embodiments, B is —$CH_2$—CH—; z is 0; and $R_5$ and $R_6$ are methyl.

In another embodiment, the polymer comprises the monomer of Formula (V) and the monomer of Formula (XI). In further embodiments, X is chlorine and M is sodium or potassium.

In another embodiment, the polymer comprises the monomer of Formula (IX) and the monomer of Formula (XI). In further embodiments, X is chlorine and M is sodium or potassium.

In further embodiments, the polymer comprises only monomers of Formula (VI), wherein X is chlorine and M is sodium or potassium.

In further embodiments, the polymer comprises only monomers of Formula (IX), wherein X is chlorine and M is sodium or potassium.

A process for making the polymer of Formula (VI) is also disclosed. The process comprises:
  providing polystyrene;
  sulfonating the polystyrene to produce polystyrene sulfonic acid;
  chlorinating the sulfur atom to produce polystyrene sulfonyl chloride;
  reacting the polystyrene sulfonyl chloride with ammonia to amidate the sulfur atom; and
  halogenating the nitrogen atom to produce the polymer of Formula (VI).

DETAILED DESCRIPTION

Halo active aromatic sulfonamide organic compounds have been known and used for over one hundred years. Chloramine-T is an example of an old sulfonamide organic compound which has been used in many applications. The usefulness of Chloramine-T is predicated on its ability to release an active Cl+ ion when needed on demand, immediately after which, it simultaneously generates an active aromatic sulfo nitrene companion ion. For example, the active Cl+ ion starts the conversion process of the odor molecule, it is immediately assisted by the companion aromatic sulfo nitrene which completes the conversion process. This process makes the halo active aromatic sulfonamides useful as odor control agents, biocides, fungicides, drugs for cultured fish, stain removal agents, and teat cleansers.

The halo active aromatic sulfonamide compounds as used in this application exhibit enhanced biocidal properties. In addition, many of these compounds have very low toxicity properties which make them attractive for use around human, animal and aquatic environments.

The polymer of the present disclosure comprises a monomer of the following Formula (I):

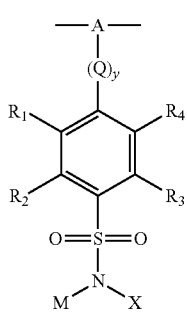

Formula (I)

wherein A is a trivalent linkage;
wherein Q is a divalent linkage and y is 0 or 1;
wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen; and
wherein M is an alkali or alkaline earth metal.

In a first specific embodiment of Formula (I), $R_1$, $R_2$, $R_3$, and $R_4$ are hydrogen or alkyl; y is 0; X is chlorine, bromine, fluorine, or iodine; and M is an alkali or alkaline earth metal. In a further specific embodiment, X is chlorine and M is sodium or potassium.

In a second specific embodiment of Formula (I), $R_1$, $R_2$, $R_3$, and $R_4$ are hydrogen or alkyl; Q comprises an ester (—COO—) linkage where the ester carbon is attached to the benzene group and y is 1; X is chlorine, bromine, fluorine, or iodine; and M is an alkali or alkaline earth metal. In a further specific embodiment, X is chlorine and M is sodium or potassium.

In other specific embodiments, A is —$CH_2$—CH—.

In other specific embodiments, Q is a methyl formate (—COO—$CH_2$—) linkage where the —$CH_2$— is attached to A (not the benzene group) and y is 1.

In a further embodiment, the polymer of the present disclosure has the following Formula (II):

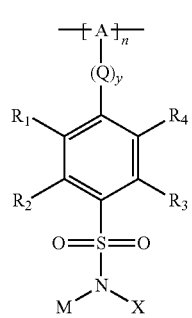

Formula (II)

wherein A is a trivalent linkage;
wherein Q is a divalent linkage and y is 0 or 1;
wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen;
wherein M is an alkali or alkaline earth metal; and
wherein n is the degree of polymerization.

In a first specific embodiment of Formula (II), $R_1$, $R_2$, $R_3$, and $R_4$ are hydrogen or alkyl; y is 0; X is chlorine, bromine, fluorine, or iodine; and M is an alkali or alkaline earth metal. In a further specific embodiment, X is chlorine and M is sodium or potassium.

In a second specific embodiment of Formula (II), $R_1$, $R_2$, $R_3$, and $R_4$ are hydrogen or alkyl; Q comprises an ester (—COO—) linkage where the ester carbon is attached to the benzene group and y is 1; X is chlorine, bromine, fluorine, or iodine; and M is an alkali or alkaline earth metal. In a further specific embodiment, X is chlorine and M is sodium or potassium.

In other specific embodiments, A is —$CH_2$—CH—.

In other specific embodiments, Q is a methyl formate (—COO—$CH_2$—) linkage where the —$CH_2$— is attached to A (not the benzene group) and y is 1.

The polymer may have any polymeric form. For example, the polymer may be a linear polymer, a nonlinear (branched) polymer, a crosslinked polymer, a copolymer, a graft copolymer, or a block copolymer. Similarly, the polymer may comprise only one monomer or several monomers. However, at least one monomer must allow attachment of or subsequent development of the aromatic N-sulfonamide moiety.

The backbone of the polymer comprises a monomer which allows attachment of or subsequent development of the aromatic N-sulfonamide moiety as a pendant group. The simplest backbone is a polyaliphatic backbone such as poly(ethylene), poly(vinyl alcohol), or poly(allyl alcohol). The backbone may also comprise other monomers which do not contain the aromatic N-sulfonamide moiety.

In specific embodiments, the polymer comprises a monomer of the following Formula (III):

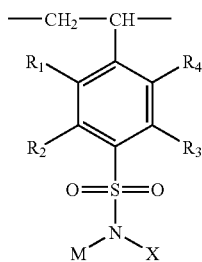

Formula (III)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen; and
wherein M is an alkali or alkaline earth metal.

In further specific embodiments, the polymer is of the following Formula (IV):

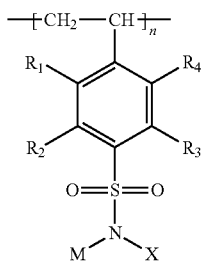

Formula (IV)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen;
wherein M is an alkali or alkaline earth metal; and
wherein n is the degree of polymerization.

In specific embodiments, the polymer comprises a monomer of the following Formula (V):

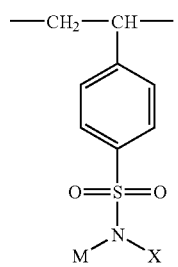

Formula (V)

wherein X is chlorine, bromine, fluorine, or iodine;
M is an alkali or alkaline earth metal; and
wherein n is the degree of polymerization.

In a more specific embodiment of Formula (V), X is chlorine and M is sodium or potassium.

In specific embodiments, the polymer has the following Formula (VI):

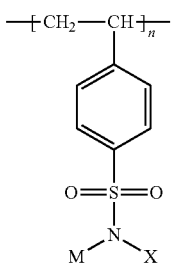

Formula (VI)

wherein X is chlorine, bromine, fluorine, or iodine;
M is an alkali or alkaline earth metal; and
wherein n is the degree of polymerization.

In a more specific embodiment of Formula (VI), X is chlorine and M is sodium or potassium.

In other specific embodiments, the polymer comprises a monomer of the following Formula (VII):

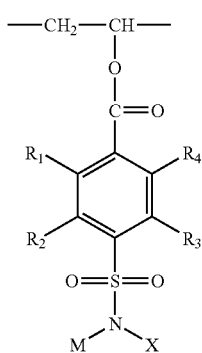

Formula (VII)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen; and
wherein M is an alkali or alkaline earth metal.

In further specific embodiments, the polymer is of the following Formula (VIII):

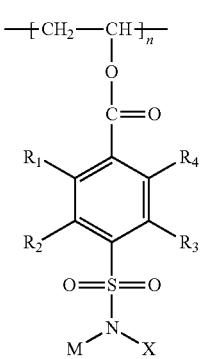

Formula (VIII)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$ or derivatized $SO_3R$, halogen, substituted or unsubstituted phenyl, sulfonamide, halosulfonamide, and linear or branched alkyl from $C_1$ to $C_{12}$, wherein the same straight or branched aliphatic moiety may be substituted at one or more of the aliphatic hydrogens;
wherein X is halogen;
wherein M is an alkali or alkaline earth metal; and
wherein n is the degree of polymerization.

In other specific embodiments, the polymer comprises a monomer of the following Formula (IX):

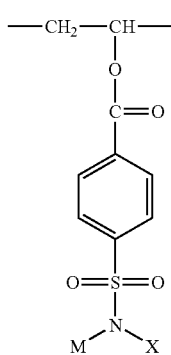

Formula (IX)

wherein X is chlorine, bromine, fluorine, or iodine;
M is an alkali or alkaline earth metal; and
wherein n is the degree of polymerization.

In a further specific embodiment of Formula (IX), X is chlorine and M is sodium or potassium.

In specific embodiments, the polymer has the following Formula (X):

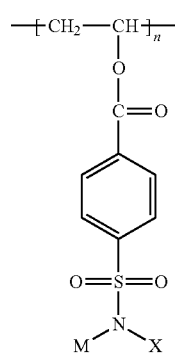

Formula (X)

wherein X is chlorine, bromine, fluorine, or iodine;
M is an alkali or alkaline earth metal; and
wherein n is the degree of polymerization.

In a further specific embodiment of Formula (X), X is chlorine and M is sodium or potassium.

It should be clear that the monomers and polymers shown in Formulas (III) through (X) are all specific embodiments of the monomer and polymer shown in Formulas (I) and (II).

The polymer of the present disclosure may be manufactured using known processes. For example, the polymer of Formula (VI) can be produced by the sulfonation of polystyrene to make polystyrene sulfonic acid. This step is described in *Turk. J. Chem.*, vol. 29, issue 2 (2005), pp. 17-123 as having a yield of 90 to 95% sulfonation. The sulfur atom can then be chlorinated to make polystyrene sulfonyl chloride, which is then reacted with ammonia to form the amide; the resulting product is poly(p-ethyl benzenesulfonamide). Finally, the poly(p-ethyl benzene sulfonamide) is halogenated to form poly(N-halo p-ethyl benzene sulfonamide) of Formula (VI). When the poly(p-ethyl benzene sulfonamide) is halogenated with MOCl at a basic pH, the M is automatically added and water is formed as a byproduct. The polymer of Formula (VI) is essentially a polymeric equivalent of Chloramine-T with the advantage that it can be removed from aqueous or gaseous media after reaction and be regenerated.

As another example, the polymer of Formula (X) is the polymeric equivalent of p-(N-halo sulfonamide) benzoic acid. The carboxylic acid moiety reacts with a pendant alcohol group to form the ester linkage of the pendant aromatic N-halo sulfonamide group.

The polymer of the present disclosure is suitable for odor control as a source of Cl+ cations. In contrast to perfumes, which merely mask odors, the polymer of the present disclosure reacts with the odor-causing molecules. The odor causing molecules are degraded by reaction with the Cl+ cation and with the sulfonamide moiety which remains after the Cl+ cation is removed from the pendant sulfonamide group.

Bleach (NaOCl) is a common source of Cl+ cations (Cl+ refers to the fact that the chlorine atom has a +1 formal charge). However, bleach has several associated problems, i.e. the discoloration of the substrate and heavy, non-discrete oxidizing power. In comparison, the Cl+ cation of the polymer, prior to release by the active aromatic N-halo sulfonamide moiety, is relatively covalent. This relative covalency assists to prevent the Cl+ ion from prematurely reacting and as such prevents the polymer from having detrimental bleaching properties.

When compared to bleach, the polymers of the present disclosure are superior deodorizing agents because they are more selective and more covalent. Further the backbone, remaining after Cl+ cations are released from the polymers of the present disclosure, reacts with the odor containing molecule, thereby permanently removing it as a potential source of odor. In contrast, the chemical moiety which remains after the Cl+ cation is removed from bleach has no ability to react with odor causing molecules.

Most odor causing molecules are mercaptans, sulfides heterocyclic or amine based compounds. The polymers of the present disclosure are excellent agents for eliminating odors from these classes of compounds as both the Cl+ cations produced by the polymers of the present disclosure and the backbone remaining after the Cl+ cations are produced, react with the odor causing molecule(s).

The polymers of the present disclosure may also function as biocides with minimal undesirable side effects. A particularly beneficial property is the fact that the polymers are nontoxic to humans, but toxic to the unwanted organisms. As a result of this nontoxicity, they can be used in proximity to humans with generally no ill effects.

The polymers of the present disclosure may be used to by placing the polymer into a liquid solution (either aqueous or solvent). In the liquid solution, the polymer acts in the same manner as Chloramine-T, generating Cl+ cations and a reactive polymer backbone which cleanse the solution. The liquid solution can then be used as an odor control agent, biocide, or fungicide by placing the liquid solution in contact with the substrate to be cleansed. The liquid solution can also be used as a teat cleanser for dairy cows by applying the solution to the teat area. Alternatively, the polymer can be wetted, for example with water, and then rubbed on the substrate like a sponge.

The amount of polymer used to form the liquid solution may vary. Generally, the amount of polymer should be sufficient to provide an equivalent of about 50 to about 600 ppm of the pendant aromatic N-halo sulfonamide group in the liquid solution. Alternatively, the polymer can be added to the liquid solution in an amount of from about 0.01 to about 20 weight percent, based on the total weight of the liquid and the polymer.

Sulfonamide compounds in the form of Chloramine T have been used, for decades, to cure diseases in cultured fish. The diseases cured are bacterial infections in the gills of fish which are contained in a rearing pond.

The polymer may also be used in a process for disease control or curing fish which are from suffering PGD. PGD is a term used to refer to a plurality of diseases, which are caused by exposure of the fish to gamma negative bacteria, myxobacteria, alromonads and pseudomonods. PGD results from crowding in the ponds or tanks which are used to contain the fish; once started a disease can spread rapidly causing the loss of millions of fish as may be contained in a tank or pond. Fish which are diseased with PGD tend to stop eating, lose their orientation and float on their side. If action is not taken immediately the whole population of the tank or pond can be dead within 24 to 48 hours. While Chloramine T has been used in the past to treat fish which are afflicted with PGD, the use of Chloramine T is difficult as if the dosages of Chloramine T are not carefully controlled the Chloramine T will kill the fish which are being treated. In the instant process, the polymer is placed in a liquid solution and the diseased fish are allowed to swim in this solution. It has been found that the polymers of the present disclosure The polymers of the present disclosure may be used to disinfect or cleanse a gaseous medium by placing the polymer in the gaseous medium for a period sufficient to allow reaction between the pendant N-halo sulfonamide groups and any molecules or bacteria in the gas.

After being used, the polymer is in a consumed state wherein the N-halo sulfonamide moieties do not contain a halogen atom and/or a metal atom. The polymer may then be separated from the medium it has cleansed and discarded. The polymer may also be hydrolyzed and regenerated by rehalogenating the nitrogen atom. The polymer can be regenerated and reactivated by simple treatment with bleach.

In some embodiments, the polymer is placed in a liquid solution containing a wetting agent. To be effective as an odor control agent, the liquid solution must come into contact with the substance which is responsible for the odor. The substance which is responsible for the odor may be in an environment which makes access difficult, i.e. pet stains in a carpet. In many instances when aqueous solution is used as a delivery medium the solution tends to bead up on the substrate. Therefore, when the water component of the solution evaporates the substance in solution is deposited only in localized areas. In the case at hand, if the liquid solution containing a polymer of the present disclosure were applied to a carpet containing pet stains, the solution would bead up on the carpet, such that when the water evaporated the placement of the compound in question on the carpet would be spotty. Due to this poor placement the reactive components of the polymer would not be in position to react with all of the odor causing substance on a molecular basis. That is, the reaction of the odor control compound with the pet stain would be incomplete, and hence the odor control would be incomplete. Thus, a wetting agent is added to the liquid solution to reduce surface tension.

Suitable substances which are useful for reducing the surface tension are synthetic and natural wetting agents. Wetting agents are generally classified as cationic, anionic, amphoteric and nonionic. Generally, the most preferred wetting agents for use in the liquid solution are anionic wetting agents, with the next preferred class of wetting agent being nonionic wetting agents. Amphoteric and cationic wetting agents are least preferred. Regardless of the above comments satisfactory agents may be found in any class of wetting agents.

While the applicant is not sure of all ramifications of how different wetting agents degrade the Cl+ moiety, functional groups such as alkenes, alcohol, ketone, especially aliphatic ketones or aldehydes containing at least one alpha hydrogen next to the carbonyl carbon are particularly detrimental to the Cl+ ion. Further phenols as may be contained on the base wetting agent molecule are particularly harmful to the Cl+ moiety.

Further while it is impossible for the applicant to explore all the ramifications thereof, impurities as may be contained in various commercially available wetting agents can play a significant part in the degradation of the Cl+ moiety. Impurities which are known to facilitate the degradation of the Cl+ moiety are aromatic and conjugated phenols, compounds containing activated carbonyl, alpha aliphatic hydrogens or active primary and secondary amines.

The concentration of the wetting agent used in the liquid solution can be from about 0.1 to 5%. A more specific concentration for the wetting agent is from about 0.5 to about 1.5%. A factor in choosing the concentration of the wetting agent is the degree to which it foams. If undesirable foaming occurs, anti-foamers may be added to the solution.

For stability and for optimum performance, the pH of a solution in which the polymer is placed should be between 6-14, with a more preferred pH range being between 8-9.5 with a most preferred range being between 8.5-9. Below a pH of 6, the activity of the polymer tends to decompose due to the acidic nature of the medium.

The polymers of the present disclosure exhibit excellent stability at a pH range of 8-9.5. This stability is important in domestic applications, where long shelf life is desirable.

It has been found that the biocidal effect of sulfonamide compounds (i.e., non-polymeric) is synergistically enhanced when the sulfonamide compound is combined with a low molecular weight alcohol in a solution. However, this effect is limited. Alcohols which do not contain hydrogen atoms alpha to the —OH moiety appear to offer more stable formulations. Alpha hydrogen atoms appear to reduce stability due to interaction with the active halogen contained in the active aromatic halo sulfonamide. Specific alcohols which are suitable for use include tertiary alcohols such as t-butanol.

Similarly, the biocidal effect of the polymers of the present disclosure may be synergistically enhanced if the polymer also comprises a monomer having a tertiary alcohol as a pendant group. Again, the monomer having the tertiary alcohol pendant group may be in the same backbone as the monomer having the N-halo sulfonamide moiety or it may be in the other polymer in a copolymer. In specific embodiments, the monomer having a tertiary alcohol as a pendant group has the following formula (XI):

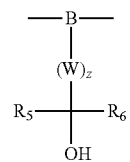

Formula (XI)

wherein B is a trivalent linkage;
wherein W is a divalent linkage and z is 0 or 1; and
wherein $R_5$ and $R_6$ are independently selected from linear or branched alkyl from $C_1$ to $C_{12}$.

W may be any divalent linkage. For example, W may be alkyl, alkoxy, ester, or ether.

In a specific embodiment, B is —CH$_2$—CH—; z is 0; and R$_5$ and R$_6$ are methyl.

In embodiments, the polymer of the present disclosure comprises the monomer of Formula (I) and the monomer of Formula (XI).

In other specific embodiments, the polymer of the present disclosure comprises the monomer shown in Formula (V) and the monomer of Formula (XI). In a further embodiment, the two monomers are in the same polymeric backbone.

In other specific embodiments, the polymer of the present disclosure comprises the monomer shown in Formula (IX) and the monomer of Formula (XI). In a further embodiment, the two monomers are in the same polymeric backbone.

The polymers of the present disclosure can be used in several settings. The polymers can be used to deodorize and then be discarded. For example, the polymers could be used in a furnace filter. Odorous molecules are neutralized as they pass through the filter. When the polymer is completely consumed, a new filter can be inserted. The polymer can also be used and regenerated. For example, the polymer can be used in a water purification column. After the water is decontaminated, the degraded column can be regenerated by circulating bleach through the column. Similarly, the polymer can be used to decontaminate beer by passing the beer through a column. Generally, the polymers of the present disclosure can be used wherever Cl+ cations would be useful and conditions do not permit direct use of liquid solutions. Such conditions would include, for example, where people will contact the liquid solution; where heat is present (evaporating the liquid solution); where it would be inconvenient to apply liquid solutions; and where a long exposure time is needed.

The present disclosure has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A polymer comprising a monomer of the following Formula (I):

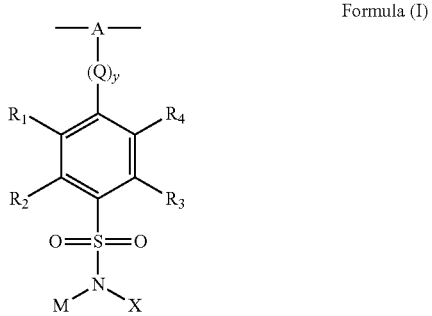

Formula (I)

wherein A is a trivalent linkage;

wherein Q is a divalent linkage and y is 0 or 1;

wherein R$_1$, R$_2$, R$_3$, and R$_4$ are independently selected from hydrogen, CF$_3$, COOH, derivatized COOH, an ester or alkylated amide, COOM, CN, NO$_2$, SO$_3$H, halogen, substituted or unsubstituted phenyl, sulfonamide, halosulfonamide, and linear or branched alkyl from C$_1$ to C$_{12}$, wherein the linear or branched alkyl moiety may be substituted at one or more of the aliphatic hydrogens;

wherein X is halogen; and wherein M is an alkali or alkaline earth metal.

2. The polymer of claim 1, wherein y is 1 and Q comprises an ester linkage.

3. The polymer of claim 1, wherein R$_1$, R$_2$, R$_3$, and R$_4$ are independently selected from hydrogen or alkyl from C$_1$ to C$_{12}$; X is chlorine, bromine, fluorine, or iodine; and M is sodium or potassium.

4. The polymer of claim 1, having the following Formula (II):

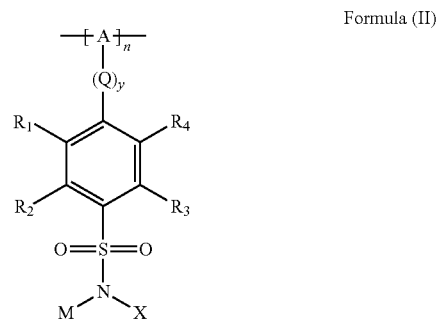

Formula (II)

wherein A is a trivalent linkage;

wherein Q is a divalent linkage and y is 0 or 1;

wherein R$_1$, R$_2$, R$_3$, and R$_4$ are independently selected from hydrogen, CF$_3$, COOH, derivatized COOH, an ester or alkylated amide, COOM, CN, NO$_2$, SO$_3$H, halogen, substituted or unsubstituted phenyl, sulfonamide, halosulfonamide, and linear or branched alkyl from C$_1$ to C$_{12}$, wherein the linear or branched alkyl moiety may be substituted at one or more of the aliphatic hydrogens;

wherein X is halogen;

wherein M is an alkali or alkaline earth metal; and wherein n is the degree of polymerization.

5. The polymer of claim 1, wherein the monomer of Formula (I) has the following Formula (III):

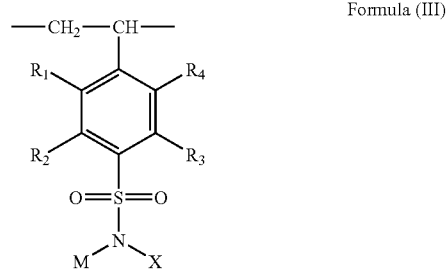

Formula (III)

wherein R$_1$, R$_2$, R$_3$, and R$_4$ are independently selected from hydrogen, CF$_3$, COOH, derivatized COOH, an ester or alkylated amide, COOM, CN, NO$_2$, SO$_3$H, halogen, substituted or unsubstituted phenyl, sulfonamide, halosulfonamide, and linear or branched alkyl from C$_1$ to C$_{12}$, wherein the linear or branched alkyl moiety may be substituted at one or more of the aliphatic hydrogens;

wherein X is halogen; and wherein M is an alkali or alkaline earth metal.

6. The polymer of claim 1, having the following Formula (IV):

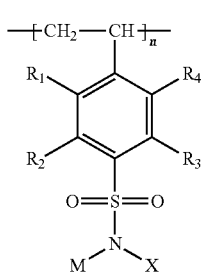

Formula (IV)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$, halogen, substituted or unsubstituted phenyl, sulfonamide, halosulfonamide, and linear or branched alkyl from $C_1$ to $C_{12}$, wherein the linear or branched alkyl moiety may be substituted at one or more of the aliphatic hydrogens;

wherein X is halogen;

wherein M is an alkali or alkaline earth metal; and wherein n is the degree of polymerization.

7. The polymer of claim 1, wherein the monomer of Formula (I) has the following Formula (V):

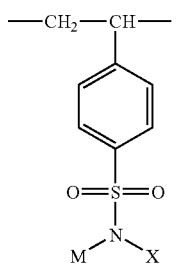

Formula (V)

wherein X is chlorine, bromine, fluorine, or iodine; and

M is an alkali or alkaline earth metal.

8. The polymer of claim 1, having the following Formula (VI):

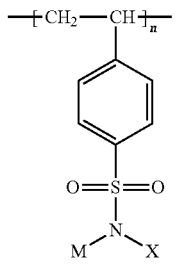

Formula (VI)

wherein X is chlorine, bromine, fluorine, or iodine;

M is an alkali or alkaline earth metal; and wherein n is the degree of polymerization.

9. The polymer of claim 1, wherein the monomer of Formula (I) has the following Formula (VII):

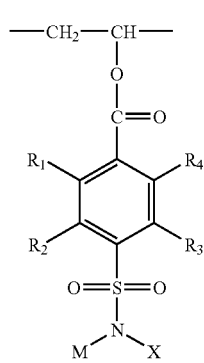

Formula (VII)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$, halogen, substituted or unsubstituted phenyl, sulfonamide, halosulfonamide, and linear or branched alkyl from $C_1$ to $C_{12}$, wherein the linear or branched alkyl moiety may be substituted at one or more of the aliphatic hydrogens;

wherein X is halogen; and wherein M is an alkali or alkaline earth metal.

10. The polymer of claim 1, having the following Formula (VIII):

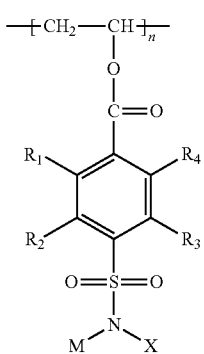

Formula (VIII)

wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$, halogen, substituted or unsubstituted phenyl, sulfonamide, halosulfonamide, and linear or branched alkyl from $C_1$ to $C_{12}$, wherein the linear or branched alkyl moiety may be substituted at one or more of the aliphatic hydrogens;

wherein X is halogen;

wherein M is an alkali or alkaline earth metal; and wherein n is the degree of polymerization.

11. The polymer of claim 1, wherein the monomer of Formula (I) has the following Formula (IX):

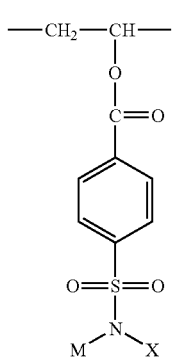

Formula (IX)

wherein X is chlorine, bromine, fluorine, or iodine; and

M is an alkali or alkaline earth metal.

12. The polymer of claim 1, having the following Formula (X):

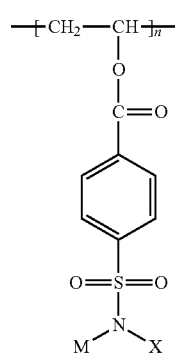

Formula (X)

wherein X is chlorine, bromine, fluorine, or iodine;

M is an alkali or alkaline earth metal; and wherein n is the degree of polymerization.

13. The polymer of claim 1, further comprising a monomer of the following Formula (XI):

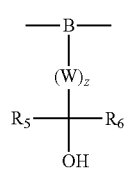

Formula (XI)

wherein B is a trivalent linkage;

wherein W is a divalent linkage and z is 0 or 1; and wherein $R_5$ and $R_6$ are independently selected from linear or branched alkyl from $C_1$ to $C_{12}$.

14. The polymer of claim 13, wherein B is —$CH_2$—CH—; z is 0; and $R_5$ and $R_6$ are methyl.

15. The polymer of claim 1, comprising a monomer of Formula (V) and a monomer of Formula (XI):

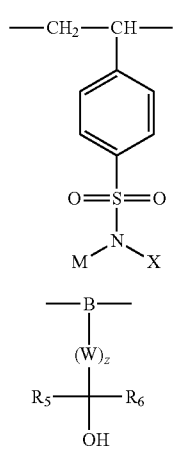

Formula (V)

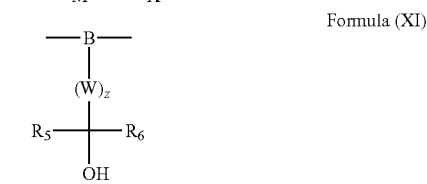

Formula (XI)

wherein X is chlorine, bromine, fluorine, or iodine;

M is an alkali or alkaline earth metal;

wherein B is a trivalent linkage;

wherein W is a divalent linkage and z is 0 or 1; and wherein $R_5$ and $R_6$ are independently selected from linear or branched alkyl from $C_1$ to $C_{12}$.

16. The polymer of claim 15, wherein X is chlorine and M is sodium or potassium.

17. The polymer of claim 1, comprising a monomer of Formula (IX) and a monomer of Formula (XI):

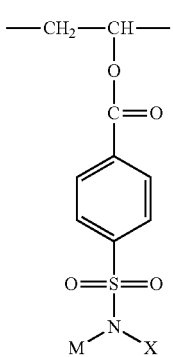

Formula (IX)

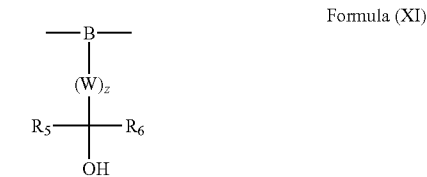

Formula (XI)

wherein X is chlorine, bromine, fluorine, or iodine;

M is an alkali or alkaline earth metal;

wherein B is a trivalent linkage;

wherein W is a divalent linkage and z is 0 or 1; and wherein $R_5$ and $R_6$ are independently selected from linear or branched alkyl from $C_1$ to $C_{12}$.

18. The polymer of claim 17, wherein X is chlorine and M is sodium or potassium.

19. A polymer having the following Formula (VI):

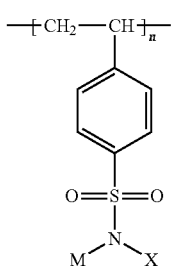

Formula (VI)

wherein X is chlorine; M is sodium or potassium; and n is the degree of polymerization.

20. A polymer having the following Formula (X):

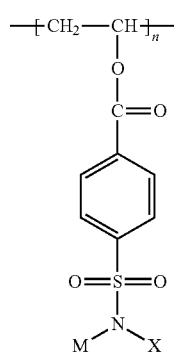

Formula (X)

wherein X is chlorine; M is sodium or potassium; and n is the degree of polymerization.

21. A process for making a polymer having the following Formula (VI):

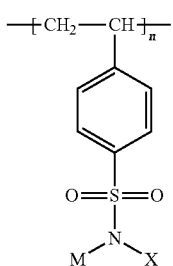

Formula (VI)

wherein X is chlorine; M is sodium or potassium; and n is the degree of polymerization, the process comprising:
providing polystyrene;
sulfonating the polystyrene to produce polystyrene sulfonic acid;
chlorinating the sulfur atom to produce polystyrene sulfonyl chloride;
reacting the polystyrene sulfonyl chloride with ammonia to amidate the sulfur atom; and
halogenating the nitrogen atom with an alkali metal hypohalide to produce the polymer of Formula (VI).

22. A process for eliminating the odor in an substrate, comprising:
providing a liquid solution comprising (i) a solvent or an aqueous medium; and (ii) a polymer having an aromatic N-halo sulfonamide pendant group, the polymer comprising a monomer of the following Formula (I):

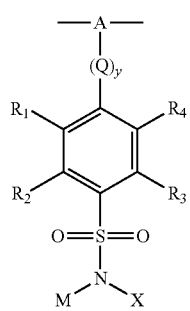

Formula (I)

wherein A is a trivalent linkage;
wherein Q is a divalent linkage and y is 0 or 1;
wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$, halogen, substituted or unsubstituted phenyl, sulfonamide, halosulfonamide, and linear or branched alkyl from $C_1$ to $C_{12}$, wherein the linear or branched alkyl moiety may be substituted at one or more of the aliphatic hydrogens;
wherein X is halogen; and
wherein M is an alkali or alkaline earth metal; and
applying the liquid solution to the substrate.

23. The process of claim 22, wherein A is —$CH_2$—CH—; y is 0; $R_1$, $R_2$, $R_3$, and $R_4$ are hydrogen; X is chlorine; and M is sodium or potassium.

24. The process of claim 22, wherein A is —$CH_2$—CH—; y is 1 and Q comprises an ester linkage; $R_1$, $R_2$, $R_3$, and $R_4$ are hydrogen; X is chlorine; and M is sodium or potassium.

25. A process for killing bacteria or fungi contained on a substrate, comprising:
providing a liquid solution comprising (i) a solvent or an aqueous medium; and (ii) a polymer having an aromatic N-halo sulfonamide pendant group, the polymer comprising a monomer of the following Formula (I):

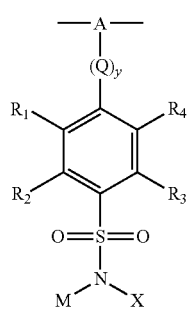

Formula (I)

wherein A is a trivalent linkage;
wherein Q is a divalent linkage and y is 0 or 1;
wherein $R_1$, $R_2$, $R_3$, and $R_4$ are independently selected from hydrogen, $CF_3$, COOH, derivatized COOH, an ester or alkylated amide, COOM, CN, $NO_2$, $SO_3H$, halogen, substituted or unsubstituted phenyl, sulfonamide, halosulfonamide, and linear or branched alkyl from $C_1$ to $C_{12}$, wherein the linear or branched alkyl moiety may be substituted at one or more of the aliphatic hydrogens;
wherein X is halogen; and
wherein M is an alkali or alkaline earth metal; and
applying the liquid solution to the substrate.

26. The process of claim 25, wherein A is —CH$_2$—CH—; y is 0; R$_1$, R$_2$, R$_3$, and R$_4$ are hydrogen; X is chlorine; and M is sodium or potassium.

27. The process of claim 25, wherein A is —CH$_2$—CH—; y is 1 and Q comprises an ester linkage; R$_1$, R$_2$, R$_3$, and R$_4$ are hydrogen; X is chlorine; and M is sodium or potassium.

28. The process of claim 25, wherein the liquid solution further comprises a wetting agent.

29. The process of claim 28, wherein the concentration of the wetting agent is from about 0.1% to 5%.

30. The process of claim 25, wherein the pH of the liquid solution is between 6 and 14.

31. A process for sanitizing the teats of a bovine, comprising:

providing a liquid solution comprising (i) a solvent or an aqueous medium; and (ii) a polymer having an aromatic N-halo sulfonamide pendant group, the polymer comprising a monomer of the following Formula (I):

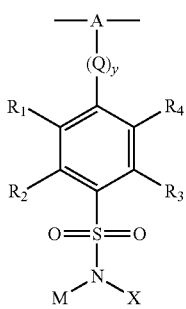

Formula (I)

wherein A is a trivalent linkage;

wherein Q is a divalent linkage and y is 0 or 1;

wherein R$_1$, R$_2$, R$_3$, and R$_4$ are independently selected from hydrogen, CF$_3$, COOH, derivatized COOH, an ester or alkylated amide, COOM, CN, NO$_2$, SO$_3$H, halogen, substituted or unsubstituted phenyl, sulfonamide, halosulfonamide, and linear or branched alkyl from C$_1$ to C$_{12}$, wherein the linear or branched alkyl moiety may be substituted at one or more of the aliphatic hydrogens;

wherein X is halogen; and wherein M is an alkali or alkaline earth metal; and applying the liquid solution to a teat of a bovine.

32. The process of claim 31, wherein A is —CH$_2$—CH—; y is 0; R$_1$, R$_2$, R$_3$, and R$_4$ are hydrogen; X is chlorine; and M is sodium or potassium.

33. The process of claim 31, wherein A is —CH$_2$—CH—; y is 1 and Q comprises an ester linkage; R$_1$, R$_2$, R$_3$, and R$_4$ are hydrogen; X is chlorine; and M is sodium or potassium.

34. A process for curing diseased fish of bacterial infections, comprising:

providing a liquid solution comprising (i) a solvent or an aqueous medium; and (ii) a polymer having an aromatic N-halo sulfonamide pendant group, the polymer comprising a monomer of the following Formula (I):

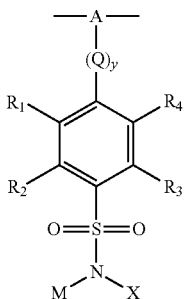

Formula (I)

wherein A is a trivalent linkage;

wherein Q is a divalent linkage and y is 0 or 1;

wherein R$_1$, R$_2$, R$_3$, and R$_4$ are independently selected from hydrogen, CF$_3$, COOH, derivatized COOH, an ester or alkylated amide, COOM, ON, NO$_2$, SO$_3$H, halogen, substituted or unsubstituted phenyl, sulfonamide, halosulfonamide, and linear or branched alkyl from C$_1$ to C$_{12}$, wherein the linear or branched alkyl moiety may be substituted at one or more of the aliphatic hydrogens;

wherein X is halogen; and wherein M is an alkali or alkaline earth metal; and allowing the diseased fish to swim in the liquid solution for an effective amount of time.

35. The process of claim 34, wherein A is —CH$_2$—CH—; y is 0; R$_1$, R$_2$, R$_3$, and R$_4$ are hydrogen; X is chlorine; and M is sodium or potassium.

36. The process of claim 34, wherein A is —CH$_2$—CH—; y is 1 and Q comprises an ester linkage; R$_1$, R$_2$, R$_3$, and R$_4$ are hydrogen; X is chlorine; and M is sodium or potassium.

37. A process for killing bacteria or fungi contained on a substrate, comprising:

providing a polymer having an aromatic N-halo sulfonamide pendant group, the polymer comprising a monomer of the following Formula (I):

Formula (I)

wherein A is a trivalent linkage;

wherein Q is a divalent linkage and y is 0 or 1;

wherein R$_1$, R$_2$, R$_3$, and R$_4$ are independently selected from hydrogen, CF$_3$, COOH, derivatized COOH, an ester or alkylated amide, COOM, CN, NO$_2$, SO$_3$H, halogen, substituted or unsubstituted phenyl, sulfonamide, halosulfonamide, and linear or branched alkyl from C$_1$ to C$_{12}$, wherein the linear or branched alkyl moiety may be substituted at one or more of the aliphatic hydrogens;

wherein X is halogen; and wherein M is an alkali or alkaline earth metal;
wetting the polymer with a liquid; and
rubbing the substrate with the polymer.

38. The process of claim 37, wherein A is —$CH_2$—CH—; y is 0; $R_1$, $R_2$, $R_3$, and $R_4$ are hydrogen; X is chlorine; and M is sodium or potassium.

39. The process of claim 37, wherein A is —$CH_2$—CH—; y is 1 and Q comprises an ester linkage; $R_1$, $R_2$, $R_3$, and $R_4$ are hydrogen; X is chlorine; and M is sodium or potassium.

* * * * *